United States Patent [19]  [11] 4,154,850
Morgan et al.  [45] May 15, 1979

[54] CERTAIN DI-(SUBSTITUTED PHENOXY) ALKANES AND HYPOLIPIDAEMIC USE THEREOF

[75] Inventors: Brian Morgan, Reigate; Keith H. Baggaley, Redhill; Richard M. Hindley, Reigate, all of England

[73] Assignee: Beecham Group Limited, England

[21] Appl. No.: 821,772

[22] Filed: Aug. 4, 1977

[30] Foreign Application Priority Data

Aug. 27, 1976 [GB] United Kingdom .............. 35680/76

[51] Int. Cl.$^2$ .................. A61K 31/235; C07C 69/76

[52] U.S. Cl. .................. 424/308; 260/600 R; 260/609 R; 260/612 R; 424/282; 424/304; 424/317; 424/324; 424/331; 424/333; 424/341; 424/309; 560/18; 560/55; 560/64; 560/65; 562/432; 562/473; 260/340.5 R; 260/465 F; 260/559 S; 260/559 T; 260/569; 260/590 D

[58] Field of Search .................. 560/55, 18, 64, 65; 424/308, 309, 282, 304, 317, 324, 331, 333, 341; 260/410.5, 340.5 R, 465 F, 559 S, 559 T, 569, 590 D, 600 R, 609 R, 612 R; 562/432, 473

[56] References Cited

U.S. PATENT DOCUMENTS 3,716,644  2/1973  Albers et al. .................. 424/308
3,983,164  9/1976  Thorne et al. .................. 560/55

*Primary Examiner*—V. D. Turner
*Attorney, Agent, or Firm*—Jacobs & Jacobs

[57] ABSTRACT

A class of di-(substituted phenoxy) alkanes having from 7 to 25 carbon atoms in the alkane moiety have hypolipidaemic activity.

10 Claims, No Drawings

CERTAIN DI-(SUBSTITUTED PHENOXY) ALKANES AND HYPOLIPIDAEMIC USE THEREOF

This invention relates to compounds which have hypolipidaemic activity, to a method for their preparation and to pharmaceutical compositions containing them.

Our British Patent Specification No. 1,482,195 discloses a class of compounds of formula (I) as having hypolipidaemic activity:

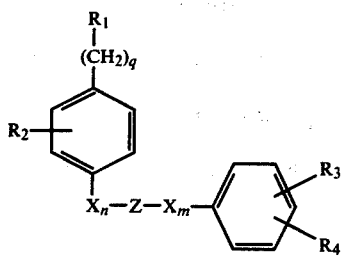

wherein
$R_1$ is a carboxylic acid group or a salt, ester or hydrazide of a carboxylic acid group; an alkyl group, optionally substituted with one or more hydroxyl groups; a nitrile, formyl, $C_{1-6}$alkanoyl or carboxyl-substituted $C_{1-6}$ alkanoyl group;
$R_2$ is a hydrogen atom, a lower alkyl group or a lower alkoxyl group;
$R_3$ is a hydrogen or halogen atom, or a lower alkyl or lower alkoxyl group;
$R_4$ is a hydrogen or halogen atom, or a phenyl; lower alkyl, lower alkoxyl, halo-lower alkyl, or nitro group; or
$R_3$ and $R_4$ together form the residue of a fused benzene ring;
Z is oxygen or sulphur;
X is a straight or branched lower-alkylene, lower-alkylene-oxy, lower-alkylene-thio, or lower-alkylene-carbonyl group;
q is zero or an integer from 1–12; and one of m and n is zero and the other is one.

One sub-group of compounds within the parent application has the structure (II):

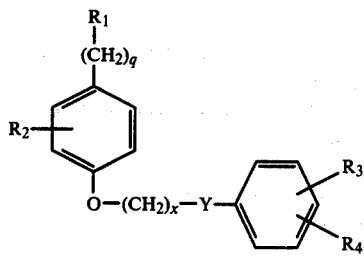

wherein $R_1$, $R_2$, $R_3$, $R_4$ and q are as defined above with respect to formula (I), x is an integer from 1 to 6 and Y is oxygen or sulphur.

Within the class of compounds of formula (I) and of formula (II) the hypolipidaemic activity of course varies from individual compound to compound, and in particular there is no correlation between the value of the integer x and the hypolipidaemic activity of the compound. We have now found that if the integer x is increased beyond six, the hypolipidaemic activity of the compounds are unexpectedly improved.

Accordingly the present invention provides a compound of formula (III):

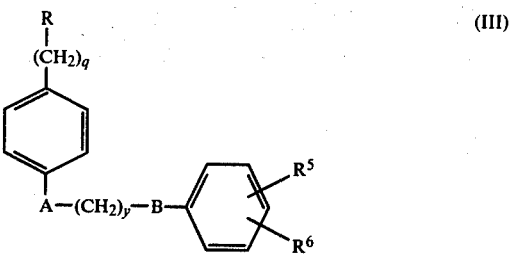

wherein
R is a carboxylic acid or a salt, ester, amide or hydrazide thereof; an alkyl group, optionally substituted with one or more hydroxyl groups; a nitrile, formyl, $C_{1-6}$alkylcarbonyl, or carboxyl or esterified carboxyl-substituted $C_{1-6}$alkylcarbonyl group.
q is zero or an integer from 1–12;
A and B represent oxygen or sulphur;
y is an integer from 7 to 25;
$R^5$ is hydrogen, halogen, $C_1$–$C_6$alkyl, or $C_1$–$C_6$alkoxy; and
$R^6$ is hydrogen, halogen, $C_1$–$C_6$alkylamino, halo-($C_1$–$C_6$)-alkyl, or carboxylic ester group, or $R^5$ and $R^6$ when on adjacent carbon atoms together represent a methylene dioxy group.

When the group R is a salt of a carboxylic acid group, suitable salting ions include metal ions e.g. aluminium alkali-metal ions such as sodium or potassium, alkaline earth metal ions such as calcium or magnesium, and ammonium or substituted ammonium ions for example those from lower alkylamines, such as triethylamine, hydroxy-lower alkylamines such as 2-hydroxyethylamine, bis-(2-hydroxyethyl)-amine or tri-(2-hydroxyethyl)-amine, cycloalkylamines such as bicyclohexylamine, or from procaine, dibenzylamine, N,N-dibenzylethylenediamine, 1-ephenamine, N-ethylamine, N,N'-bis-dehydroabietylethylenediamine, or bases of the pyridine type such as pyridine, collidine or quinoline.

Suitable esters include alkyl, cycloalkyl, alkenyl, alkynyl, aryl, aralkyl or heterocyclic groups, any of which may be substituted. Suitable such groups include:
(a) alkyl especially $C_{1-6}$alkyl such as methyl, ethyl n-and iso-propyl, n-, sec-, iso and tert-butyl, and pentyl;
(b) substituted $C_{1-6}$alkyl wherein the substituent is at least one of: chloro, bromo, fluoro, nitro, carbo ($C_{1-6}$)alkoxy, $C_{1-6}$alkanoyl, $C_{1-6}$alkoxy, cyano, $C_{1-6}$alkylmercapto, $C_{1-6}$alkylsulfinyl, $C_{1-6}$alkylsulphonyl, 1-indanyl, 2-indanyl, furyl, pyridyl, 4-imidazolyl, phthalimido, azetidino, aziridino, pyrrolidino, piperidino, morpholino, thiomorpholino, N-($C_{1-6}$alkyl)-piperazino, pyrrolo, imidazolo, 2-imidazolino, 2,5-dimethylpyrrolidino, 1,4,5,6-tetrahydropyrimidino, 4-methylpiperidino, 2,6-dimethylpiperidino, alkylamino, dialkylamino, alkanoylamino, N-alkylanilino, or substituted N-alkylanilino wherein the substituent is chloro, bromo, $C_{1-6}$alkyl or $C_{1-6}$alkoxy;
(c) cycloalkyl and ($C_{1-6}$alkyl) substituted cycloalkyl having from 3 to 7 carbon atoms in the cycloalkyl moiety;
(d) alkenyl having up to 8 carbon atoms;
(e) alkynyl having up to 8 carbon atoms;

(f) phenyl and substituted phenyl wherein the substituent is at least one of chloro, bromo, fluoro, $C_{1-6}$alkoxy, $C_{1-6}$alkanoyl, carbo-($C_{1-6}$)alkoxy, nitro, or di($C_{1-6}$) alkyl amino;

(g) benzyl or substituted benzyl wherein the substituent is chloro, bromo, fluoro, $C_{1-6}$alkyl, $C_{1-6}$alkoxy, $C_{1-6}$alkanoyl, carbo-($C_{1-6}$)alkoxy, nitro, or di($C_{1-6}$alkyl)amino;

(h) a 5- or 6- membered heterocyclic group containing one or more sulphur and/or nitrogen and/or oxygen atoms in the ring optionally fused to a second 5- or 6- membered hydrocarbyl or heterocyclic ring and which may be substituted with an alkyl group having 1 to 3 carbon atoms, for example thienyl, furyl quinolyl, methyl-substituted quinolyl, phenazinyl, pyridyl, methylpyridyl, phthalidyl, indanyl, imidazolyl, thiadiazolyl, isoxazolyl, methylisoxazolyl, tetrazolyl, methyltetrazolyl, pyrimidinyl, pyridyl, pyrazinyl, pyrrolidyl, piperidyl, morpholinyl, or thiazinyl.

Preferred ester groups are $C_1$-$C_6$alkyl groups especially methyl and ethyl.

Other suitable groups R include alkyl groups (especially straight chain alkyl groups containing an odd number of carbon atoms); alkyl groups substituted by one or more hydroxyl groups such as hydroxymethyl or 1- or 2-hydroxyethyl.

In one preferred class of compounds, the moiety —$(CH_2)_qR$ is a group which is converted in the body to a carboxymethyl group of formula —$CH_2CO_2H$. For example when q is an odd integer R may be carboxyl, or a salt or ester thereof; or when q is an even integer R may be an acetyl group of formula —$CO.CH_3$. In one preferred combination, R is an acetyl group and q is 2.

Suitable $C_1$-$C_6$alkyl groups for $R^5$ and $R^6$ include methyl, ethyl and straight and branched chain propyl and butyl groups.

Suitable $C_{1-6}$alkoxy groups for $R^5$ and $R^6$ include methoxy and ethoxy groups.

A preferred haloalkyl group for $R^6$ is the trifluoromethyl group.

Preferably $R^5$ is hydrogen and $R^6$ is hydrogen, $C_{1-6}$alkyl or halogen; especially chlorine.

The integer y may be from 7 to 25 but is preferably in the range 9 to 16, especially 10 to 14.

Preferably both A and B are oxygen.

One sub-class of compounds within the present invention is represented by formula (IV):

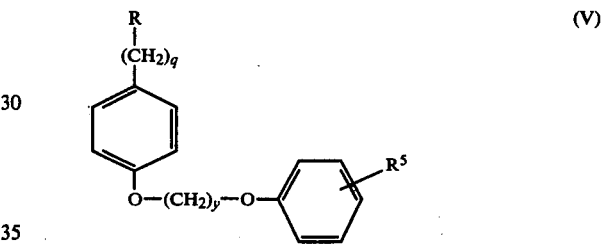
(IV)

wherein R, $R^5$, $R^6$ and y are as defined with respect to formula (III).

Preferably $R^6$ represents hydrogen and $R^5$ is in the 4-position.

Specific compounds of formula (IV) include:

n-1-(4-ethoxycarbonylphenoxy)-7-(4-chlorophenoxy)-heptane;
n-1-(4-ethoxycarbonylphenoxy)-8-(4-chlorophenoxy)-octane;
n-1-(4-ethoxycarbonylphenoxy)-9-(4-chlorophenoxy)-nonane;
n-1-(4-ethoxycarbonylphenoxy)-10-(4-chlorophenoxy)-decane;
n-1-(4-ethoxycarbonylphenoxy)-11-(4-chlorophenoxy)-undecane;
n-1-(4-ethoxycarbonylphenoxy)-12-(4-chlorophenoxy)-dodecane;
n-1-(4-ethoxycarbonylphenoxy)-13-(4-chlorophenoxy)-tridecane;
n-1-(4-ethoxycarbonylphenoxy)-14-(4-chlorophenoxy)-tetradecane;
n-1-(4-ethoxycarbonylphenoxy)-15-(4-chlorophenoxy)-pentadecane;
n-1-(4-ethoxycarbonylphenoxy)-20-(4-chorophenoxy)-eicosane;
n-1-(4-ethoxycarbonylphenoxy)-10-(4-fluorophenoxy)-decane;
n-1-(4-ethoxycarbonylphenoxy)-10-(4-methoxyphenoxy)decane;
n-1-(4-acetylphenoxy)-12-(4-chlorophenoxy)-dodecane.

A further group of compounds having good hypolipidaemic activity is represented by formula (V):

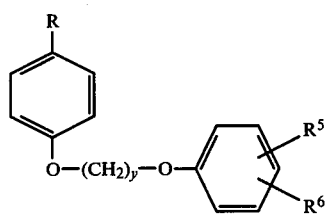
(V)

wherein R, $R^5$ and y are as defined with respect to formula (III), and q is from 1 to 6.

Examples of compounds of formula (V) wherein q is 1 are:

1-(4-ethoxycarbonylmethylphenoxy)-7-(4-chlorophenoxy)-heptane; and
1-(4-ethoxycarbonylmethylphenoxy)-10-(4-chlorophenoxy)-decane.

Examples of compounds of formula (V) wherein q is 2 are:

1-(4-β-ethoxycarbonylethylphenoxy)-10-(4-chlorophenoxy)-decane; and
1-(4-β-ethoxycarbonylethylphenoxy)-12-(4-chlorophenoxy)-dodecane.

A further sub-class of compounds of this invention is represented by formula (VI):

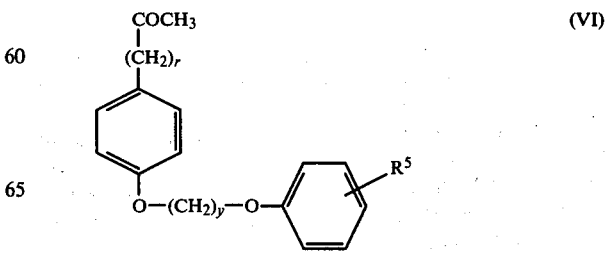
(VI)

wherein $R^5$ and y are as defined with respect to formula (III) above and r is an even integer. Preferably r is 2 4 or 6.

An example of a compound of formula (VI) is: 1-[4-(β-acetylethyl)phenoxy]-10-[4'-chlorophenoxy]-decane.

The compounds of this invention may be prepared by reacting a compound of formula (VII):

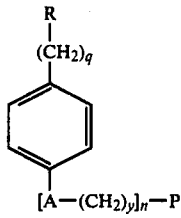 (VII)

with a compound of formula (VIII):

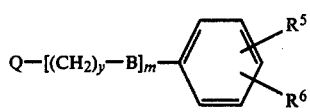 (VIII)

wherein R, $R^5$, $R^6$, A, B, q and y are as defined with respect to formula (III); one of n and m is one and the other is zero; P represents —AH [where A is defined with reference to formula (III)] or a reactive derivative thereof when n is zero or is a readily displaceable group when n is 1; and q represents —BH [where B is defined with reference to formula (III)] or a reactive derivative thereof when m is zero or is a readily displaceable group when m is 1; and optionally thereafter converting at least one group R, $R^5$ and $R^6$ to a different such group.

Reactive derivatives of the groups —AH and —BH include salts thereof and other derivatives which increase the nucleophilicity of the atom A or B.

By a "readily dispalceable group" is meant an atom or group which is displaceable by a nucleophilic centre (such as the lone pair electrons on a hydroxyl oxygen or alkoxide ion). Such groups include halides such as iodine, bromine or chlorine; pseudo-halides such as the azido group $N_2$—; active esters such as the groups —O.$SO_2CH_3$, $O.CO.OC_2H_5$; compounds prepared in situ from dehydrating agents such as carbodiimides or carbonyldiimidazoles, phosphorus pentachloride, phosphoryl chloride, thionyl chloride, or phosphorus pentoxide; or other such good leaving groups.

For the preparation of compounds wherein A or B is oxygen the group —AH or —BH is a hydroxyl group. If the hydroxyl compound used in the above condensation reaction is in the form of a salt, it is generally in the form of the sodium or potassium salt.

When the condensation reaction uses a salt as one of the reactants, the salt is preferably produced by means of a strong base, for example, sodium hydride, sodamide, or a sodium alkoxide or sodium methoxide. Suitable solvents for the reaction include dimethylformamide or dimethylsulphoxide (especially when employing sodium hydride or sodamide as base), methanol (when using sodium methoxide) and ethanol (when using sodium ethoxide).

It may be preferable to modify the substituents R, $R^5$ and/or $R^6$ after the condensation reaction rather than before. Thus, it is preferable, when preparing compounds of formula (III) wherein R includes an amide or carboxylic acid group, first to prepare the corresponding compound with a carboxylic acid ester group and then to convert such group to carboxylic acid group or amide by conventional means.

Similarly, if the group R contains a hydroxyl group, it may be advantageous to first protect it by forming a readily hydrolysable ester which can be removed subsequent to the condensation reaction.

Alternative methods of preparing compounds wherein R contains an ester group include the esterification of the free acid or its salt or other reactive derivative of the acid, or transesterification of a compound having a different ester group. Esterification may be performed by any conventional method, for example by reaction of the free acid: (a) with the appropriate alcohol in the presence of a catalyst such as a strong acid, dry hydrogen chloride, or p-toluenesulphonic acid; or (b) with the appropriate halide or sulphate of the alcohol in the presence of dimethylsulphoxide and calcium carbonate or with the halide in the presence of hexamethylphosphoramide or (c) by phase transfer catalysis methods with the halide and/or sulphate of the alcohol in aqueous and/or organic solution in the presence of a quaternary ammonium salt such as tetrabutyl ammonium bisulphate or halide, or benzyltrimethylammonium halide.

The formation of compounds (III) wherein R is an ester may also be carried out by conventional transesterification methods, for example reaction of an ester with the appropriate second alcohol in the presence of a catalyst such as the sodium salt of the alcohol, or dry hydrogen chloride, p-toluenesulphonic acid, or potassium cyanide.

Compounds of formula (III) wherein R is an ester may also be prepared by alkanolysis of the corresponding nitrile (R=CN); or by hydrolysis of an iminoether compound having formula (III) wherein R is a group of formula:

wherein $R_a$ is the hydrocarbon residue of an alcohol or phenol.

Compounds wherein R contains a carboxyl group may be prepared by oxidation of the corresponding precursor having formula (III) wherein R is selected from:
(a) formyl;
(b) methyl;
(c) hydroxymethyl;
(d) vinyl, or substituted vinyl;
(e) acyl Examples of the reagents which may be employed to effect such oxidations include respectively,
(a) basic silver oxide, or concentrated nitric acid;
(b) acidic sodium or potassium dichromate;
(c) manganese dioxide followed by basic silver oxide;
(d) aqueous potassium permanganate in an organic solvent such as benzene in the presence of a quaternary ammonium salt such as a tetrabutylammonium halide;
(e) a hypohalite. The acryl group may be an acetyl group ($CH_3CO$). Preferable the hypohalite reactant is sodium hypohalite which may be generated in situ in aqueous solution by the reaction of sodiumhydroxide on a mixture of iodine and potassium iodide. The desired free acid may be isolated and converted to any desired salt by known methods.

Compounds wherein R contains a carboxylic acid group can also be prepared by the acid or base catalysed hydrolysis of the corresponding compound of formula (III) wherein R is selected from:

(a) carboxylic acid amide group;
(b) nitrile group (—CN);
(c) esterified carboxylic acid group Hydrolysis of amides may be carried out using a mineral acid as catalyst, suitably hydrochloric acid or sulphuric acid. Base catalysed hydrolysis may be carried out using an alkali metal or alkaline earth metal hydroxide, e.g. sodium or potassium hydroxide. Suitably the hydrolysis reaction is carried out in aqueous solution and fairly severe reaction conditions are preferred, e.g. refluxing for several hours. The desired compound can be isolated as the free acid by neutralisation of the resultant reaction mixture or as the appropriate base addition salt (e.g. sodium salt if sodium hydroxide was employed) or acid addition salt (e.g. the hydrochloride if HCl was employed.). Alternatively the free acid can be converted to any desired salt by standard procedures.

For the hydrolysis of a compound wherein R is a nitrile group, ammonia is liberated and thus the preferred catalyst is an acid which will bind the ammonia e.g. a hydrogen halide such as HCl or HBr. If base catalysed hydrolysis is used, ammonia is liberated and the acid will be obtained as an alkali salt, or, after neutralisation, as the free acid.

For the hydrolysis of an esterified carboxylic acid group, preferably the process involves hydrolysis with a strong base such as sodium hydroxide. The esterified carboxylic acid groups R may be, for example lower alkoxycarbonyl groups such as methoxycarbonyl or tertiary butoxycarbonyl groups. The remarks made earlier about salts of the resultant free acid also apply in this case.

A further method for the preparation of compounds of formula (III) wherein R is a carboxylic acid group comprises the carbonation of a compound of formula (II) wherein R is a group of formula:

—MX followed by hydrolysis, wherein M is magnesium, calcium or lithium and X is chlorine, bromine or iodine. Such reagents are of course well known in the art and may be prepared by known methods. Carbonation is preferably carried out using gaseous carbondioxide but solid carbon dioxide may be used on occasions. Hydrolysis of the intermediate formed after carbonation can be carried out simply by the addition of water.

Compounds of formula (III) wherein R is a hydroxymethyl group may be prepared by reduction of the compound wherein R is a formyl or ester group.

An alternative method for the preparation of the compounds of this invention comprise the reduction of a compound of formula (IX):

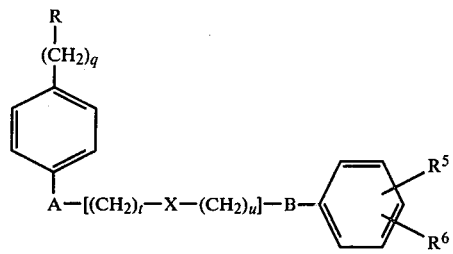

wherein R, q, A, B, $R^5$ and $R^6$ are as defined with respect to formula (III) above, X represents either a carbonyl group,

or an alkynl group, —C≡C—, and t and u are integers such that the total number of carbon atoms in the group $[(CH_2)_t—X— (CH_2)_u]$ is from 7 to 25, Any suitable method of reduction may be used depending on the nature of X and which does not reduce other moieties in the molecule. A suitable method when X is carbonyl, is the action of an alkali metal borohydride reagent, such as sodium cyanoborohydride on a corresponding hydrazone of compound (IX).

When X is alkynyl, a convenient method of reduction of compound (IX) is catalytic hydrogenation, for example in the presence of platinum oxide.

The hypolipidaemic compounds according to the invention may be formulated for administration in any convenient way using techniques known in the art. The present invention therefore also provides a pharmaceutical composition comprising a compound of formula (III) above together with a pharmaceutical carrier or excipient.

The compositions may be formulated for administration by any route, although an oral administration is preferred. The compositions may be in the form of tablets, capsules, powders, granules, lozenges, or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol, or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as dry product for reconstitution with water or other suitable vehicle before use. Such liquid preparations may contain conventional additives such as suspending agents, for example sorbitol, syrup, methyl cellulose, glucose syrup, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired convention flavouring or colouring agents.

Suppositories will contain conventional suppository bases, e.g. cocoa, butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle.

The compound may be administered alone in combination with one or more pharmaceutically acceptable carriers, or as part of the total dietary intake. In the latter case, the amount of said compound may be less than 1% by weight of the diet and is preferably no more than 0.5% by weight. The diet for a man may consist of normal food stuffs to which the ester has been added, and similarly the diet for animals may consist of food stuffs and the compound may be added alone or with a premix.

In order to achieve an effective degree of serum-lipid lowering, the compound should preferably be administered to the animal or patient in an amount of from 1 to 10 g. per day; generally it will be most convenient to spread the daily dosage by giving several smaller more palatable doses.

The following examples illustrate the preparation of some of the compounds of this invention.

EXAMPLE 1 n-1-(4-Ethoxycarbonylphenoxy-7-(4-chlorophenoxy)-heptane

Sodium (2.5 g., 0.11 M) was dissolved in absolute ethanol (50 ml) and ethyl 4-hydroxybenzoate (16.6 g., 0.10 M) in ethanol (50 ml) was added at room temperature. The mixture was stirred at room temperature for 15 min, 1-bromo-7-(4-chlorophenoxy)-heptane (0.10 M) in ethanol (50 ml) was added in one portion and the mixture was boiled under reflux with stirring for 24 hours. The hot solution was filtered to remove sodium bromide, the ethanol removed under vacuum, the product dissolved in dichloromethane (100 ml) and washed with 5% sodium hydroxide solution (2×100 ml) and water (2×100 ml). The dichloromethane solution was dried (MgSO₄), filtered, evaporated and the product purified by crystallisation, from ethanol m.p. 70°-71°.

EXAMPLES 2-13.

The following compounds were prepared by a method substantially as described in Example 1:

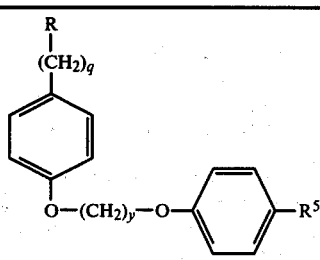

| Example No. | R | q | y | R⁵ | m.p. (°C.) | Purification method* |
|---|---|---|---|---|---|---|
| 2 | CO$_2$C$_2$H$_5$ | 0 | 8 | Cl | 61–62 | a |
| 3 | CO$_2$C$_2$H$_5$ | 0 | 9 | Cl | 65–66 | a |
| 4 | CO$_2$C$_2$H$_5$ | 0 | 10 | Cl | 68 | a |
| 5 | CO$_2$C$_2$H$_5$ | 0 | 12 | Cl | 67–9 | b |

-continued

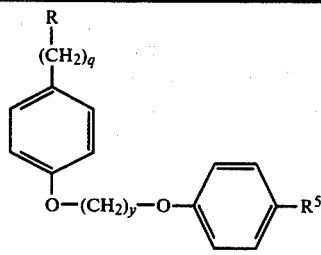

| Example No. | R | q | y | R⁵ | m.p. (°C.) | Purification method* |
|---|---|---|---|---|---|---|
| 6 | CO$_2$C$_2$H$_5$ | 0 | 10 | F | 59–61 | b |
| 7 | CO$_2$C$_2$H$_5$ | 1 | 7 | Cl | 46 | b |
| 8 | CO$_2$C$_2$H$_5$ | 1 | 10 | Cl | 54 | a |
| 9 | CO$_2$C$_2$H$_5$ | 2 | 10 | Cl | 55 | b |
| 10 | CO$_2$C$_2$H$_5$ | 2 | 12 | Cl | 60–61 | a |
| 11 | COCH$_3$ | 2 | 10 | Cl | 75 | a |
| 12 | CO$_2$C$_2$H$_5$ | 0 | 10 | OCH$_3$ | 89–91 | b |
| 13 | COCH$_3$ | 0 | 12 | Cl | | |

*a : purification by crystallisation by ethanol
b : purification by chromatography.

EXAMPLE 14

1-(4-Ethoxycarbonylphenoxy)-13-(4-chlorophenoxy)-tridecane

A mixture of 1-(4-chlorophenoxy)-13-tridecanol (3.27 g.; 0.01 M.), ethyl 4-hydroxybenzoate (2.49 g.; 0.015 M) and dicyclohexylcarbondiimide (3.09 g.; 0.015 M.) was heated at 100°–105° C. for 5 hours with stirring. The reaction mixture was cooled to room temperature, dichloromethane was added and the mixture was filtered. The filtrate was evaporated to dryness under reduced pressure and the crude product (5.95 g.) was chromatographed on silica-gel (250 g.) in dichloromethane to give 1-(4-ethoxycarbonylphenoxy)-13-(4-chlorophenoxy)-tridecane (1.82 g.; 38%). M.P. 75°–7° C.

EXAMPLE 15

1-(4-Ethoxycarbonylphenoxy)-11-(4-chlorophenoxy)-undecane was prepared by a method substantially as described in Example 14, m.p. 94°–95° C.

EXAMPLE 16

1-(4-Ethoxycarbonylphenoxy)-15-(4-chlorophenoxy)-pentadecane (a) Sodium (0.69 g; 0.03 M.) was dissolved in absolute ethanol (30 ml.) with protection from atmospheric moisture. Ethyl 4-hydroxybenzoate (4.98 g; 0.03 M.) in absolute ethanol (20 ml.) was added and the mixture was stirred at room temperature for 30 minutes. A solution of 1-bromo-15-(4-chlorophenoxy)-pentadecan-11-one (8.62 g. 0.02 M.) in absolute ethanol (30 ml.) was added and the mixture was boiled under reflux with stirring for 8 hours. After cooling to room temperature dichloromethane (200 ml.) was added, the mixture was extracted with 5% sodium hydroxide solution (2×100 ml.) and water (1×100 ml.). The solution was dried (MgSO₄), the solvent evaporated under reduced pressure and the crude product (8.75 g.) was purified by chromatography on silica-gel (300 g.) in dichloromethane to give 1-(ethoxycarbonylphenoxy)-15-(4-chlorophenoxy)-pentadecan-11-one (5.07 g.; 33%), M.P. 95°–96° C.

(b) To 1-(4-ethoxycarbonyl)-15-(4-chlorophenoxy)-pentadecan-11-one (2.07 g.; 0.004 M) in 1:1 D.M.F. - sulpholane was added tosylhydrazine (0.93 g.; 0.005 M)

and p-toluenesulphonic acid (0.12 g.). The mixture was heated at 105° C. for 1 hour with stirring, cyclohexane (8 ml.) was added at this temperature and sodium cyanoborohydride (1.01 g.; 0.016 M) was added portionwise over a period of 5 minutes. The mixture was stirred at 105° C. for 2 hours, cooled to room temperature and added to iced-water (70 ml). Extraction with cyclohexane (2×100 ml.) followed by drying (MgSO$_4$) and evaporation of the solvent under reduced pressure yielded a gummy material (1.40 g.) which on chromatography on silica-gel (50 g.) in dichloromethane gave 1-(4-ethoxycarbonylphenoxy)-15-(4-chlorophenoxy) pentadecane (1.20 g; 60%) M.P. 84°–85° C.

EXAMPLE 17

1-(4-Ethoxycarbonylphenoxy)-14-(4-chlorophenoxy)-tetradecane

To a solution of sodium (0.58 g.; 0.025 M.) in absolute ethanol (15 ml.) was added ethyl 4-hydroxybenzoate (4.15 g; 0.025 M.) in absolute ethanol (20 ml.) and the mixture was stirred at room temperature for 15 minutes. A solution of 1-bromo-14-(4-chlorophenoxy)-tetradec-9-yne (7.00 g.; 0.0175 M.) in absolute ethanol (20 ml). was added and the mixture was boiled under reflux with stirring for 6 hours. The reaction mixture was cooled to room temperature filtered and the solvent removed under reduced pressure. Dichloromethane (100 ml.) was added to the residual oil, the solution was washed with 5% sodium hydroxide solution (2×100 ml.), saturated sodium chloride solution (1×100 ml.), dried and evaporated. The oil thus produced was purified by chromatography on silica-gel (250 g.) in dichloromethane to give 1-(4-ethoxycarbonylphenoxy)-14-(4-chlorophenoxy)-tetradec-9-yne (3.76 g.; 44%) M.P. 52°–53° C.

1-(4-ethoxycarbonylphenoxy)-14-(4-chlorophenoxy)-tetradec 9-yne (2.00 g.; 0.0041 M.) in acetic acid (15 ml.) was reduced in the presence of hydrogen and PtO$_2$ (0.05 g.) at 60° C. and atmospheric pressure. When hydrogen absorption was complete the solution was filtered, the catalyst washed well with ethanol and the solvents evaporated under reduced pressure to yield a colourless oil. 1-(4-ethoxycarbonylphenoxy)-14-(4-chlorophenoxy)-tetradecane (1.62 g.; 80%) M.P. 72.5°–73.5° C. was obtained as a pure crystalline compound by chromatography of this oil on silica-gel (100 g.).

EXAMPLE 18

1-(4-Ethoxycarbonylphenoxy)-20-(4-chlorophenoxy)-eicosane was prepared by a method substantially as described in Example 17, m.p. 78°–80° C.

Biological Data

The hypocholesterolaemic and/or hypotriglyceridaemic effects of several compounds of the present invention were demonstrated in the following experiment:

Groups of 8 male albino rats (C.F.Y. strain), weighing approximately 150 g., were given a powdered commercially available diet (oxoid) to which compounds were added at level of either 0.1% or 0.25%. These diets were fed for seven days. The rats were then killed and their serum total cholesterol and triglyceride were measured by the Technicon Autoanalyser. Table 1 shows the results expressed in terms of percentage cholesterol lowering and percentage triglyceride lowering compared with controls.

| Example No. | Level in diet (%) | Percentage lowering of serum cholesterol | Percentage lowering of serum triglycerides |
|---|---|---|---|
| 1 | 0.25 | 31 | 71 |
| 2 | 0.25 | 30 | 48 |
| 3 | 0.25 | 32 | 79 |
| 4 | 0.25 | 43 | 74 |
| 5 | 0.10 | 25 | 66 |
| 6 | 0.25 | 51 | 59 |
| 8 | 0.25 | 14 | 74 |
| 9 | 0.1 | 42 | 67 |
| 10 | 0.1 | 12 | 48 |
| 11 | 0.25 | 13 | 61 |
| 14 | 0.10 | 31 | 68 |
| 15 | 0.10 | 16 | 42 |

We claim:
1. A compound of the formula

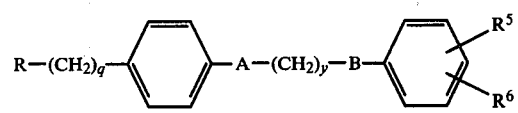

wherein
R is a free carboxylic acid group or a pharmaceutically acceptable salt or ester thereof;
q has a value of from 0 to 12; each of A and B is oxygen or sulfur;
y has a value of from 7 to 25;
R$^5$ is hydrogen, halo, alkyl of 1 to 6 carbon atoms or alkoxy of 1 to 6 carbon atoms; and R$^6$ is hydrogen, halo, alkyl of 1 to 6 carbon atoms, alkoxy of 1 to 6 carbon atoms, alkanoyloxy of 1 to 6 carbon atoms, amino, alkylamino of 1 to 6 carbon atoms, haloalkyl of 1 to 6 carbon atoms or carboalkoxy having 1 to 6 carbon atoms in the alkoxy group.

2. A compound according to claim 1 wherein y is at least 10.

3. A compound according to claim 1 wherein q is 0 and R is carboxy or carbalkoxy having 1 to 6 carbon atoms in the alkoxy group.

4. A compound according to claim 1 wherein A and B are each oxygen.

5. A compound according to claim 1 wherein R$^6$ is hydrogen and R$^5$ is hydrogen, alkoxy of 1 to 6 carbon atoms or halo.

6. A compound according to claim 5 wherein R$^6$ is in the 4-position of the depicted phenyl ring.

7. A compound according to claim 1 said compound having the formula

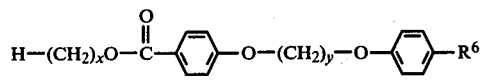

wherein
x has a value of 1 to 6
y has a value of 10 to 25 and
R$^6$ is hydrogen, chloro or methoxy, 8. A compound according to claim 7 wherein y is 10 to 14.

9. A pharmaceutical composition comprising a pharmaceutically acceptable carrier together with a hypolipidemically effective amount of at least one compound according to claim 1.

10. The method of effecting a hypolipidemic response in humans and other animals which comprises administering thereto a hypolipidemically effective amount of a compound according to claim 1.

* * * * *